United States Patent [19]
Rzeszotarski et al.

[11] Patent Number: 5,175,290
[45] Date of Patent: Dec. 29, 1992

[54] 8-(OXO-SUBSTITUTED CYCLOALKYL)XANTHINES

[75] Inventors: Waclaw J. Rzeszotarski, Millersville; Roger N. Hiner, Baltimore; Scott W. Feeney, Millersville, all of Md.

[73] Assignee: Marion Merrell Dow Inc., Kansas City, Mo.

[21] Appl. No.: 245,164

[22] Filed: Sep. 16, 1988

[51] Int. Cl.$^5$ .................. C07D 473/04; C07D 473/06; A61K 31/52
[52] U.S. Cl. ..................................... 544/267; 544/271
[58] Field of Search ................. 544/267, 271; 514/263

[56] References Cited

U.S. PATENT DOCUMENTS

| | | | |
|---|---|---|---|
| 4,612,315 | 9/1986 | Jacobson et al. | 514/263 |
| 4,696,932 | 9/1987 | Jacobson et al. | 514/263 |
| 4,755,517 | 7/1988 | Bruns et al. | 514/263 |
| 4,769,377 | 9/1988 | Snyder et al. | 514/263 |
| 4,772,607 | 9/1988 | Badger et al. | 514/263 |
| 4,783,530 | 11/1988 | Rzeszotarski et al. | 544/267 |

OTHER PUBLICATIONS

Erdnt, et al., Chemical Abstracts, vol. 86: 72,580n (1977).
Shamim, et al., Chemical Abstracts, vol. 108: 94,512s (Mar. 1988).
Shamim, et al, J. Med. Chem., vol. 31, No. 3, pp. 613–617 (Mar. 1988).

Primary Examiner—Diana G. Rivers
Attorney, Agent, or Firm—Theresa M. Gillis

[57] ABSTRACT 1,3-Substituted-8-(oxo-substituted cycloalkyl)xanthines and pharmaceutically acceptable salts of such compounds are disclosed. Preferred compounds include the cis and trans isomers of 1,3-dipropyl-8-(3-hydroxycyclopentyl)xanthine and the cis and trans isomers of 1,3-dipropyl-8-(4-hydroxycyclohexyl)xanthine. The compounds are potent and selective bronchodilators and/or cardiotonic agents.

3 Claims, No Drawings

8-(OXO-SUBSTITUTED CYCLOALKYL)XANTHINES

BACKGROUND OF THE INVENTION a) Field of the Invention

This invention relates to 8-(oxo-substituted cycloalkyl)xanthines and pharmaceutically acceptable salts thereof which possess useful and relatively potent and selective bronchodilating and cardiotonic activity. The compounds can reverse histamine-induced bronchoconstriction in guinea pigs and protect against pentobarbital-induced heart failure in rats.

b) State of the Art

Many xanthine derivatives, as exemplified by theophylline and caffeine, induce a variety of pharmacological effects, including antiasthmatic, diuretic, respiratory stimulant, central stimulant, cardiac stimulant, and analgetic adjuvant activities [J. W. Daly, J. Med. Chem. 25, 197-207 (1982)]. The central nervous system (CNS) stimulating effects of these agents include the production of nervousness, restlessness, insomnia, tremors, hyperesthesia, and other signs of CNS stimulation. At high doses they may even cause convulsions and seizures. Xanthines also activate the medullary respiratory centers where the drugs appear to increase the sensitivity of these centers to the stimulatory actions of carbon dioxide.

The xanthines also have prominent actions on the circulatory system. For example, theophylline produces modest decreases in peripheral vascular resistance, sometimes powerful cardiac stimulation, and increased perfusion of most organs that may result in diuresis. Moreover, another agent, amrinone, which is related to xanthines, is a widely used effective cardiotonic agent [A. W. Ward, R. N. Brogden, R. C. Heel, T. M. Speight and G. S. Avery, Drugs 26, 468-502 (1983); L. N. Seigel et al., Am. Heart J. 106, 1042-1047 (1983)].

A disadvantage of the use of theophylline in patients with compromised circulatory function is that it frequently causes CNS and cardiac toxicity [K. M. Piafsky, S. D. Sitar, R. E. Rango, and R. I. Ogiline, Clin. Pharmacol. Ther. 21, 310-316 (1977)]. As a result more effective vasodilators, specific inotropic agents and diuretics now find favor in clinical practice [J. N. Cohn and J. A. Franciosa, N. Engl. J. Med. 297, 254-258 (1977)]. At therapeutic doses theophylline causes modest increases in heart rate and decreases in peripheral vascular resistance, thus resulting in an increased blood flow; however, in man this effect is short-lived.

Many xanthines also cause relaxation of a variety of smooth muscles, especially smooth muscle of the bronchi which has been constricted experimentally by histamine or clinically in asthma. Theophylline is of value in the treatment of bronchial asthma where it produces a demonstrable increase in vital capacity. The effects of theophylline on the cardiovascular system and CNS, together with a narrow therapeutic window, however, reduce the effectiveness of its therapeutic utility.

The xanthines produce a number of other pharmacological effects in addition to the aforementioned ones. For example, they may increase skeletal muscle tone, an effect possibly involving $Ca^{2+}$ translocation. Moreover, xanthines have been shown to augment release of secretory products by various endocrine and exocrine tissues, whereas they have been shown to inhibit the secretion of mediators of inflammation by mast cells and other tissues.

Such diverse pharmacological effects of xanthines have been attributed to three basic cellular actions: (1) mechanisms associated with translocation of intracellular calcium, (2) effects mediated by increasing accumulation of cyclic nucleotides and (3) effects mediated by blockade of adenosine receptors [See, e.g., T. W. Rall in "Goodman and Gilman's The Pharmacological "Basis of Therapeutics", 7th Ed., A. G. Gilman, L. S. Goodman, T. W. Rall, and F. Murad, eds., MacMillan, N.Y., 1985, pp. 589-603)]. The third mechanism has received greatest attention recently; i.e., that xanthines exert their pharmacological effects primarily as adenosine receptor antagonists. There are at least two subpopulations of such receptors, designated $A_1$, which inhibit adenylate cyclase, and $A_2$, which stimulate adenylate cyclase [See, e.g., R. F. Bruns, J. W. Daly and S. H. Snyder, Proc. Natl. Acad. Sci. U.S.A. 80, 2077-2080 (1983)]. Receptor binding studies have indicated receptor heterogeneity among the $A_1$ subtype [K. M. Murphy and S. H. Snyder, Mol. Pharmacol. 22, 250-257 (1982)] as well as different tissue distributions for the receptor subtypes.

Whereas, certain xanthine derivatives demonstrate receptor selectivity, caffeine and theophylline are about equally effective in displacing ligands from both the $A_1$ and $A_2$ adenosine receptors. It is uncertain, however, whether therapeutic responses to theophylline administration in asthmatic patients involve antagonism of adenosine receptors. This uncertainty is based largely on the observation that enprofylline (3-propylxanthine), an agent that appears to be about five-fold more potent than theophylline as a bronchodilator in man and other species [C. G. A. Persson, Agents Actions 13 (Suppl.), 115-129 (1983)], is much less effective than theophylline in diminishing responses to adenosine in all tissues studied, except for the rat hippocampus [B. B. Fredholm and C. G. A. Persson, Eur. J. Pharmacol. 81, 673-676 (1982)].

The present invention provides new, potent and selective xanthines which are effective in reversing histamine-induced bronchoconstriction in guinea pigs and preventing pentobarbital-induced heart failure in rats. These new 1,3-substituted-8-(oxo-substituted cycloalkyl)xanthines have useful bronchodilating and cardiotonic activity.

SUMMARY OF THE INVENTION

This invention relates to novel 8-(oxo-substituted cycloalkyl)xanthines which are potent and selective bronchodilators and cardiotonics, relatively free of undesirable side effects. Specifically, this invention provides compounds of the formula:

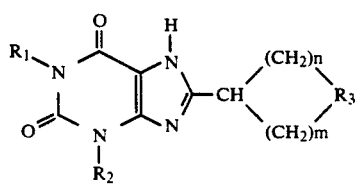

wherein
$R_1$ and $R_2$ may be the same or different and are selected from hydrogen, lower alkyl, allyl, carboxyalkyl, carbalkoxyalkyl, and aralkyl;

$R_3$ is C=O or CH—OR$_4$, wherein R$_4$ is selected from hydrogen, carbonylalkylcarboxylic acid having an alkyl bridge of 1-3 C, and related lower alkyl esters;

n is 0 to 7 and m is 1 to 7, with the proviso that n and m taken together cannot exceed 7.

The invention includes the pharmaceutically acceptable salts of compounds of the foregoing formula. The invention also relates to the use of the compounds in the treatment of respiratory and heart disorders.

DETAILED DESCRIPTION OF THE INVENTION

The compounds of the invention are those having the formula:

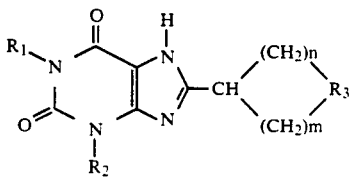

I wherein $R_1$ and $R_2$ may be the same or different and are selected from hydrogen, lower alkyl, allyl, carboxyalkyl, carbalkoxyalkyl and aralkyl;

$R_3$ is C=O or CH—OR$_4$, wherein R$_4$ is selected from hydrogen, carbonylalkylcarboxylic acid having an alkyl bridge of 1-3 C, and related lower alkyl esters;

n is 0 to 7 and m is 1 to 7, with the proviso that n and m taken together cannot exceed 7, and pharmaceutically acceptable salts of such compounds.

The invention thus encompasses compounds of the formulae:

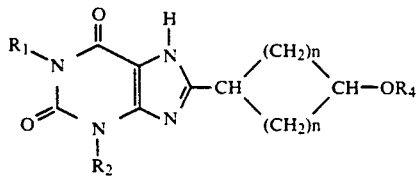

Ia and

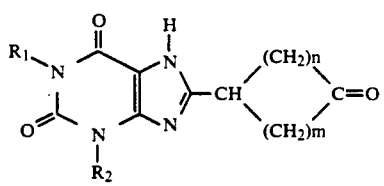

Ib with the substituents as defined above, and pharmaceutically acceptable salts of such compounds.

The terms "alkyl" and "lower alkyl" are intended to mean an alkyl group having one to six carbons. The "alkyl" portion of an "alkoxy" is meant to be an alkyl group having one to six carbons. By "aralkyl" is meant an alkyl substituted with 5- or 6-membered aromatic homocyclic or S-or O-containing heterocyclic aryl groups and includes benzyl, thienyl and furanylmethyl. Alkyl groups may be straight chain, branched, cyclic, saturated or unsaturated. The invention includes all possible geometrical and optical isomers of compounds of formula I.

Preferred compounds are those in which $R_1$ is n-propyl, $R_2$ is n-propyl, n is one or two, and m is two. The most preferred compounds are the cis and trans isomers of 1,3-dipropyl-8-(3-hydroxycyclopentyl)xanthine and the cis and trans isomers of 1,3-dipropyl-8-(4-hydroxycyclohexyl)xanthine.

The compounds of the invention are potent and selective bronchodilators and cardiotonic agents, as demonstrated by their ability to reverse histamine-induced bronchoconstriction in guinea pigs and protect against pentobarbital-induced heart failure in rats.

The invention also relates to pharmaceutical compositions containing the compounds for treating respiratory and heart disorders, such as asthma or compromised cardiac function, and to methods for treating a patient suffering from such conditions by administering a therapeutically effective amount of such compounds to the patient.

The compounds of this invention may be used in the form of pharmaceutically acceptable salts or complexes with various inorganic or organic bases. Typical salts include the alkali metal or alkaline earth salts, although it is to be appreciated that other nontoxic salts are also intended. The compounds of this invention, by virtue of the acidic proton in the 7 position, can form anions at alkaline pH and thus can be advantageously administered as sodium, potassium or ammonium salts, choline salts and complexes with ethylenediamine, for example.

The compounds of this invention may be administered orally or parenterally in conventional dosage unit forms such as tablets, capsules, injectables or the like, by incorporating the appropriate dose of a compound of the invention with carriers according to accepted pharmaceutical practices. Preferably the compound or a basic addition salt or complex thereof is administered orally to a patient in a tablet or capsule comprising an amount sufficient to produce bronchodilator or cardiotonic activity. Each dosage unit will contain the active medicament in an amount of about 10 mg to about 100 mg. Advantageously, equal doses will be administered 4 to 6 times daily to the patient, with the daily dosage regimen being about 40 mg to about 200 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be 25 mg to about 1 g. If a liquid carrier is used, the preparation will be in the form of a syrup, emulsion, soft gelatin capsule, sterile injectable liquid such as an ampule, or an aqueous or nonaqueous liquid suspension.

Of particular applicability is an aerosol dispensing system wherein the active medicament is incorporated with Freon ® (fluorohydrocarbon) or other inert propellant in an aerosol container. Such an aerosol system will deliver a metered dose of about 50 mcg to about 1600 mcg, administered as needed.

The compounds may be synthesized according to known methods. Accordingly, the appropriate hydroxyl protected cycloalkanecarboxylic acid is condensed, via the acid chloride with the requisite 1,3-disubstituted-5,6-diaminouracil, prepared, for example by the method of V. Papesch and E. F. Schroeder [J. Org. Chem. 17, 1879 (1952)], to afford an amide which is dehydratively cyclized and the hydroxyl protecting group removed to afford the 1,3-disubstituted-8-(hydroxy-substituted cycloalkyl)xanthine. The hydroxyl group is acylated with an appropriate acid halide or anhydride to give the esters indicated in formula Ia. Oxidation of the hydroxyl group, for example, with chromic anhydride in dilute sulfuric acid in acetone, provides compounds of the formula Ib.

The following examples illustrate the preparation of specific compounds of the invention with bronchodilator and/or cardiotonic activity. All temperatures and melting points (mp) are degrees Celsius (°C.) and $^1$H NMR signals are given (p.p.m.) in the indicated solvent using an internal standard of tetramethylsilane. The examples should not be construed to limit the scope of the invention as described hereinabove and as claimed.

EXAMPLE 1

Cis- and trans-8-(3-hydroxycyclopentyl)-1,3-dipropylxanthine

Oxalyl chloride (2.32 mL, 26.6 mmol) was added to a stirred solution of 3-methoxymethyloxycyclopentanecarboxylic acid (4.63 g, 26.6 mmol), dimethylformamide (0.15 mL, 1.9 mmol), and anhydrous pyridine (2.16 mL, 26.6 mmol) in dichloromethane at 5° C. under argon. The mixture was stirred at 5° C. for 15 minutes and then at room temperature for 30 minutes. After being cooled to 5° C. a solution of 5,6-diamino-1,3-dipropyluracil (6.0 g, 26.5 mmol) and pyridine (2.26 mL, 27.9 mmol) in 100 mL of dichloromethane was added. The resulting mixture was stirred at 5° C. for 30 minutes and then at room temperature for one hour. Water (100 mL) was added and the mixture was made acidic to Congo Red indicator by addition of 5N hydrochloric acid. The organic layer was separated, washed with aqueous sodium bicarbonate and brine. After being dried over sodium sulfate, the organic solution was concentrated to afford the crude amide as an amorphous yellow-orange foam.

To a solution of the crude amide in 40 mL of dioxane was added 21.8 mL (101 mmol) of 1,1,1,3,3,3-hexamethyldisilazane (HMDS) and 0.3 g (2.3 mmol) of ammonium sulfate. The mixture was stirred at reflux temperature for 18 hours, cooled to room temperature and concentrated to give a crude mixture of cis and trans-1,3-dipropyl-8-(3-methoxymethyloxycyclopentyl)xanthines as a yellow solid. A solution of this solid in 15 mL of tetrahydrofuran and 15 mL of 5N hydrochloric acid was stirred at room temperature for 48 hours. The mixture was adjusted to pH 5 with a 10% aqueous solution of sodium carbonate and extracted with chloroform. The organic extract was washed with sodium bicarbonate solution and brine. After being dried over anhydrous sodium sulfate, the chloroform solution was concentrated. Residual yellow solid was stirred with 25 mL of ether at reflux temperature for one hour. The mixture was cooled to 25° C., filtered, and dried to give an off-white solid. Purification by flash chromatography (silica gel, 9.2% ethanol in chloroform) gave 2.5 g (39%) of the "high Rf" trans-8-(3- hydroxycyclopentyl)-1,3-dipropylxanthine as a white powder, mp 173°-175° C.; TLC (silica gel, 9:1/CHCl$_3$:EtOH), Rf=0.38, IR (KBr) 3430, 3144, 1701, 1656, 1555, 1503 cm$^{-1}$; $^1$H NMR (300 MHz, CDCl$_3$) 12.5 (br s, 1H), 4.70 (br s, 1H), 4.50 (br s, 1H), 4.04 (m, 4H), 3.6 (m, 1H), 2.35-1.90 (m, 6H), 1.78 (sextet, 2H, J=7.3 Hz), 1.71 (sextet, 2H, J=7.4 Hz), 0.97 (t, 6H, J=7.3, 7.4 Hz). Identification of the trans geometry was established by 2D NMR. Anal. calcd for C$_{16}$H$_{24}$N$_4$O$_3$: C, 59.98; H, 7.55; N 17.59. Found: C, 60.07; H, 7.56; N, 17.48.

The "low Rf" cis-8-(3-hydroxycyclopentyl)-1,3-dipropylxanthine was obtained as 1.47 g (23%) of a white powder, mp 192°-193° C.; TLC (silica gel, 9:1/CHCl$_3$:EtOH) Rf=0.24; IR (KBr) 3496, 3170, 1700, 1648, 1554, 1500 cm$^{-1}$; $^1$H NMR (300 MHz, CDCl$_3$) 12.61 (s, 1H), 4.60 (m, 1H), 4.10 (t, 2H, J=7.5 Hz), 4.02 (t, 2H, 7.5 Hz), 3.67 (pentet, 1H, J=8.8 Hz), 2.20-1.90 (m, 6H), 1.90-1.60 (m, 5H), 0.97 (t, 6H, J=7.4 Hz). Cis stereochemistry was determined for this product by 2D NMR. Anal. calcd for C$_{16}$H$_{24}$N$_4$O$_3$: C, 59.98; H, 7.55; N, 17.49. Found: C, 60.06; N, 7.55; H, 7.45.

EXAMPLE 2

Cis- and trans-8-(4-hydroxycyclohexyl)-1,3-dipropylxanthine,

To a stirred solution of ethyl 4-oxocyclohexanecarboxylate (2.0 g, 12 mmol) in 10 mL of ethanol at 5° C. was added, in portions, 0.5 g (13 mmol) of sodium borohydride. After the mixture was stirred for 30 minutes at 5° C. and 18 hours at room temperature it was diluted with 10 mL of water and acidified to pH 3 with 1N hydrochloric acid. The mixture was extracted with ethyl acetate. After being washed with water and brine the extracts were dried over anhydrous sodium sulfate and concentrated to give ethyl 4-hydroxycyclohexanecarboxylate as a colorless liquid. This alcohol (2.08 g, 25 mmol) in 12 mL of 1,2-dichloroethane at room temperature was added to 4.10 mL (23.1 mmol) of N,N-diisopropylethylamine and 1.65 mL (21.7 mmol) of chloromethyl methyl ether. The resulting mixture was stirred and refluxed for 24 hours, cooled to room temperature, diluted with 20 mL of water, acidified to pH 3 with hydrochloric acid and extracted with methylene chloride (3×20 mL). The combined organic layers were washed with 1N hydrochloric acid, dried over anhydrous sulfate, and concentrated. The resulting liquid was purified by flash chromatography (silica gel, 17% ether in low boiling petroleum ether) to give 1.95 g (79.2%) of ethyl 4-methoxymethyloxycyclohexanecarboxylate. This ester (1.91 g, 8.83 mmol) was hydrolyzed by stirring with lithium hydroxide hydrate (0.75 g, 18 mmol) in a solution of methanol (20 mL) and water (5 mL) at room temperature for 24 hours. The mixture was diluted with 20 mL of water and extracted with ether. The aqueous part was acidified to the Congo Red endpoint, salted with sodium chloride, and extracted with ethyl acetate. The extract was dried over anhydrous sodium sulfate, and concentrated to give the 4-methoxymethyloxycylohexanecarboxylic acid (1.47 g, 88.6%) as a colorless liquid, IR (neat) 3500-2400 (broad), 1704 cm$^{-1}$. To a stirred solution of this acid (1 4 g, 7.44 mmol), 0.03 mL (0.4 mmol) of dimethylformamide, and 0.6 mL (7.5 mmol) of pyridine in 20 mL of methylene chloride at 5° C. under argon was added 0.67 mL (7.5 mmol) of oxalyl chloride. After the mixture was stirred for 5 minutes at 5° C. and 30 minutes at room temperature, it was added to a solution of 5,6-diamino-1,3-di-n-propyluracil (1.68 g, 7.42 mmol) and pyridine (0.7 mL, 8.7 mmol) in 15 mL of methylene chloride. After 15 minutes at 5° C. and 1 hour at room temperature the resulting solution was diluted with water (25 mL), acidified to pH 1 with 5N hydrochloric acid, and the layers were separated. The aqueous layer was extracted with methylene chloride (3×25 mL), the combined organic extracts were washed with a saturated aqueous solution of sodium bicarbonate, and dried over sodium sulfate. Concentration gave the intermediate amide as a yellow amorphous semi-solid. A stirred solution of the crude amide, hexamethyldisilazane (HMDS) (8.0 mL, 37.1 mmol), and ammonium sulfate (0.1 g, 0.76 mmol) in 20 mL of dioxane was refluxed for 19 hours. The mixture was cooled to room temperature, treated with 5 mL of methanol and stirred for 1 hour. The suspension was concentrated to dryness, the resulting solid was triturated with 25 mL of ether, filtered, washed twice with 10 mL portions of ether, twice with 10 mL portions of low boiling petroleum ether and dried in vacuo at room temperature to give a mixture (2.15 g, 76.8%) of trans and cis-1,3-di-n-propyl-8-(4-methoxymethyloxycyclohexyl)xanthine. The xanthine (1.63 g, 4.31 mmol), together with concentrated hydrochloric acid (10 drops), in 25 mL of methanol was stirred and refluxed for 18 hours. Upon cooling to room temperature, solids that precipitated from the mixture were filtered, washed with three 5 mL portions of ether and dried in vacuo at 110° C. over phosphorous pentoxide for 18 hours to give 1.03 g (75.1%) of a white solid: mp 223–225° C.; IR (KBr) cm$^{-1}$ 3417, 3149, 1700, 1653, 1553, 1499, 1393; $^1$H NMR (300 MHz, DMSO) 0.85 (m, 6H), 1.10–2.10 (m, 12H), 2.70 (m, 1H), 3.40 (m, 1H), 3.85 (m, 4H), 4.39 & 4.62 (2×d, 1H total), 13.10 (2×s, 1H total). Anal. calcd for $C_{17}H_{26}N_4O_3$: C, 61.06; H, 7.84; N, 16.75. Found: C. 61.04; H, 7.84; N, 16.72.

EXAMPLE 3

6-Amino-3-carboethoxymethyl-1-propyluracil

6-Amino-1-propyluracil (10 g, 59.1 mmol) was dissolved by warming gently in 60 mL of dimethylsufoxide. 2.0 g (66 mmol) of an 80% dispersion of sodium hydride in mineral oil was added in portions to the solution while stirring under argon. After the evolution of hydrogen ceased, the mixture was heated to 40° C. until a solution resulted. To this solution at 25° C. was added ethyl bromoacetate (7.1 mL, 62 mmol), with the mixture maintained under argon at room temperature for 44 hours. The mixture was then diluted with 200 mL of water and extracted with hexane to remove the mineral oil. The aqueous layer was adjusted to pH 10 with 3N sodium hydroxide and extracted with dichloromethane. The extracts were dried over anhydrous sodium sulfate and concentrated to a brown liquid, which was purified by flash chromatography (silica gel, 9:1/chloroform:ethanol) to yield a crystalline product.

EXAMPLE 4

6-Amino-3-carboethoxymethyl-5-nitroso-1-propyluracil

6-Amino-3-carboethoxymethyl-1-propyluracil (2.55 g, 10 mmol) is dissolved in 10 mL of acetic acid. The solution is stirred at 70° C. and a solution of 0.83 g (12 mmol) of sodium nitrite in 10 mL of water is added dropwise over a period of 10 minutes. The resulting precipitate is filtered, washed with ether and air-dried to give the nitroso derivative.

EXAMPLE 5

5,6-Diamino-3-ethoxycarbonylmethyl-1-propyluracil

6-Amino-3-carboethoxymethyl-5-nitroso-1-propyluracil (2.84 g, 10 mmol) is slurried with 75 mL of absolute ethanol and 100 mg of 10% palladium-on-carbon. The mixture is hydrogenated at 25° C. and an initial pressure of 60 p.s.i. of hydrogen in a Parr apparatus. After uptake of hydrogen is completed the mixture is filtered and the filtrate concentrated to give the diaminouracil.

EXAMPLE 6

Trans and cis-1-carboethoxymethyl-8(3-hydroxycycloheptyl)-3-propylxanthine

This compound is prepared from 5,6-diamino-3-carboethoxymethyl-1-propyluracil and the O-methoxymethyl protected derivative of 3-hydroxycycloheptanecarboxylic acid as described in Examples 1 and 2.

EXAMPLE 7

Trans and cis-1-carboxymethyl-8(3-hydroxycycloheptyl)-3-propylxanthine

A solution of trans and cis-1-carboethoxymethyl-8-(3-hydroxycycloheptyl)-3-propylxanthine (2.76 g, 10 mmol) in 25 mL of ethanol is stirred and refluxed with 1.0 g (25 mmol) of sodium hydroxide in 5 mL of water for 2 hours. The resulting solution is concentrated, mixed with water and acidified with hydrochloric acid to give the resulting xanthine-1-hydrochloric acid derivative.

EXAMPLE 8

Trans-8-(3-carboethoxymethylcarboxycyclopentyl)-1,3-dipropylxanthine

A stirred mixture of trans-8-(3-hydroxycyclopentyl)-1-3-dipropylxanthine (2.96 g, 10 mmol), ethyl malonylchloride (1.51 g, 10 mmol), and triethylamine (1.1 g, 11 mmol) in 25 mL of tetrahydrofuran is stirred at reflux temperature for 4 hours. The solution is concentrated and suspended in 100 mL of water. Insoluble product is separated by filtration.

EXAMPLE 9

Cis-8-[3-(2-carboxyethyl)carboxycyclopentyl]-1,3-dipropylxanthine

A stirred mixture of cis-8-(3-hydroxycyclopentyl)-1,3-dipropylxanthine (2.96 g, 10 mmol) and succinic anhydride (1.0 g, 10 mmol) in 25 mL of tetrahydrofuran is stirred at reflux temperature for 8 hours. After the mixture is concentrated, it is diluted with 100 mL of water and the mixture filtered to give the product.

EXAMPLE 10

1,3-Dipropyl-8-(3-oxocylopentyl)xanthine

A solution of sodium dichromate in aqueous sulfuric acid (Jones reagent) was added dropwise to a stirred solution of 1.40 g (4.37 mmol) of 1,3-dipropyl-8-(3-hydroxycyclopentyl)xanthine in 100 mL of acetone at 30° C. until the red-orange color persisted. The mixture was stirred at room temperature for 30 minutes, 3 mL of 2-propanol was added, and stirring was continued for an additional 5 minutes. The green mixture was diluted with 100 mL of water, sodium chloride was added and the mixture was extracted with ethyl acetate. The combined organic extracts were washed first with a saturated aqueous solution of sodium bicarbonate and then with brine, dried over sodium sulfate and concentrated. Residual solid was triturated with boiling ether, filtered, washed with ether and dried to give 0.79 g (57%) of a white solid: mp 160°–161° C.; IR (KBr) 3149, 1753, 1703, 1656, 1555, 1504, 1394 cm$^{-1}$; $^1$H NMR (300 MHz, CDCl$_3$) 0.97 (t, 3H, J=7.5 Hz), 0.97 (t, 3H, 7.5 Hz), 1.70 (sextet, 2H, J=7.4 Hz), 1.80 (sextet, 2H, J=7.5 Hz), 2.35 (m, 2H), 2.55 (m, 2H), 3.23 (m, 1H), 4.01 (m, 2H), 4.10 (m, 2H), 13.04 (s, 1H). Anal. calcd for $C_{16}H_{22}N_4O_3$: C, 60.36; H, 6.97; N, 17.60. Found: C, 60.12; H, 7.00; N, 17.54.

EXAMPLE 11

Reversal of histamine-induced bronchoconstriction in the anesthetized guinea pig A modification of the general method of H. Konzett and R. Rössler [Naunyn-Schmiedeberg's Arch. Pharmakol. 195, 71–74 (1940)] was used.

Male Duncan-Hartley guinea pigs (400–600) were anesthetized using an intratraperitoneal injection of urethane (1.5 g/kg). After the neck area was shaved, the animal was placed in the dorsal recumbent position on a Narco temperature controlled surgical board (37° C.) to maintain body temperature. Following a midline neck incision, the carotid artery and jugular vein were cannulated using PE50 polyethylene tubing. Both catheters were flushed with heparinized saline (20 U/mL) to prevent clotting. The trachea was then cannulated using a 15 gauge Leuer stub and was connected to a Harvard Apparatus small animal respirator. The animal was ventilated at a constant rate and volume (52 breaths/minute and 1 mL room air/100 mg body weight). Airway pressure was measured using a Statham pressure transducer connected to the side port of the tracheal cannula. The arterial blood pressure was measured using a Statham pressure transducer connected to the carotid artery. Both transducers were connected to a Gould chart recorder to produce the desired physiographs.

After allowing the animal to stabilize for 10 minutes, aerosolized histamine (0.01%) was delivered to the airways using a DeVilbiss ultrasonic nebulizer connected in-line between the respirator and the guinea pig. After the maximum bronchoconstriction was reached, as evidenced by a maximum plateau in airway pressure, an injection of vehicle (0.6 mL) was administered via the jugular vein. A dose response curve was then determined by administering the test compound via the jugular vein, beginning with the lowest dose and injecting the next higher dose immediately following the maximum airway pressure response of the preceding drug concentration. At the end of the experiment, terbutaline sulfate (1 mg/mL), a beta agonist, was injected i.v. to determine if further bronchodilation could be achieved The nebulizer was then turned off and the minimum airway pressure was recorded to determine the final baseline pressure.

ED$_{50}$ (mg/kg) values and maximum effect (%) were calculated using SAS and PROBIT computer analyses. ED$_{50}$ is the dose of the test compound required to reverse the histamine response by 50%. The maximum effect is the maximum percent reversal of histamine-induced bronchoconstriction produced by the test compound. The results are reported in the Table.

EXAMPLE 12

Pentobarbital-induced heart failure in rats

Adult male Sprague-Dawley rats (350–450 g) were used in this example. Animals were anesthetized using sodium pentobarbital (40–50 mg/kg, i.p.) and placed supine on a heated (37° C.) surgical table. A 7F pressure tipped catheter (Millar) was inserted into the left carotid artery and advanced into the left ventricle of the heart to measure left ventricular pressure (LVP), dP/dt and heart rate (HR). Mean arterial blood pressure (MABP) was monitored via a PE-50 catheter placed into a femoral artery. The right jugular vein and a femoral vein were catheterized with PE-10 tubing for infusion of the test compounds and pentobarbital, respectively.

Following bilateral cervical vagotomy, a 15 gauge blunt needle was inserted into the trachea via a midcervical tracheostomy to ventilate the animals (60/minute, TV=2.3 mL) Each animal was allowed a 5–10 minute period to stabilize and control measurements were recorded. A dose of 60–70 mg/kg of pentobarbital wa then administered slowly over a 5 minute period via the femoral vein until MABP was stabilized at 60 mm Hg, at which time an infusion of 0.2 mg/kg/minute of pentobarbital was begun and continued throughout the experiment. Each animal was then allowed 10–15 minutes to stabilize and values representing heart failure were recorded. Control and test compounds were tested in a cumulative-dose manner using at least four doses. Dose-related effects, e.g., dP/dt and MABP were continually monitored during a 15 minute recovery period between each dose. At the time of the peak dP/dt response during each recovery period, values for all four variables were recorded. The animals were sacrificed using a lethal injection of pentobarbital 15 minutes following the last dose of the test compound. Only one compound was administered to each animal.

The RD$_{40}$ is defined as the dose of compound required to achieve a 40% recovery in the variable (dP/dt, MABP) being measured. It was calculated for each compound using an SAS ® probit analysis on a Vax computer. Briefly, the program transforms the dose into log 10 and calculates the line of least squares using the mean value for recovery at each dose. In most instances the RD$_{40}$ was then extrapolated, but in those instances where a full dose-response curve was not achieved because of the limited solubility of the compound, the RD$_{40}$ was estimated.

Results of the test compounds and controls are presented in the Table.

EXAMPLE 13

Cardiovascular effects (basal heart rate and basal blood pressure) in guinea pigs Male guinea pigs were anesthetized with urethane and the carotid artery and jugular vein were cannulated. Aortic blood pressure was recorded from a pressure transducer and the signal was integrated to give a heart rate signal.

Each animal received a single intravenous injection of one compound. The dose of each compound was based upon the ED$_{50}$ value from the reversal of histamine-induced bronchoconstriction in the anesthetized guinea pig. Thus the various compounds were studied at equipotent bronchodilator doses (2×ED$_{50}$). A group of control animals received injections of vehicle only. Changes in heart rate and blood pressure from pre-injection baseline values produced by drugs or vehicle were compared. The data are presented in the Table.

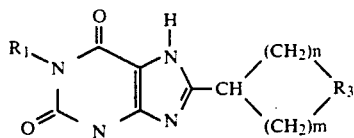

TABLE

Pharmacological properties of some 8-(oxo-substituted cycloalkyl)xanthines and bronchodilator and cardiotonic standards

| FORMULA Ia | | | | | | Histamine-induced bronchoconstriction, reversal, guinea pigs. ED$_{50}$, mg/kg. i.v. (maximum effect, %) | Cardiovascular effects at 2 × histamine-reversal ED$_{50}$, guinea pigs. i.v. | | Pentobarbital-induced heart failure, rats | | |
|---|---|---|---|---|---|---|---|---|---|---|---|
| R$_1$ | R$_2$ | R$_4$ | n | m | Isomer | | Basal heart rate, % | Basal Blood pressure, % | RD$_{40}$, dP/dt, mg/kg. i.v. (maximum recovery %) | RD$_{40}$, MABP, mg/kg. i.v. (maximum recovery %) | RD$_{40}$, heart rate mg/kg, i.v. (maximum recovery dose, mg/kg. i.v.) |
| n-Pr | n-Pr | H | 1 | 2 | trans | 11.6 ± 1.6 (78.5 ± 4.0) | 107 ± 5* | 96 ± 8* | 7.8 (71) | ** | 3.1 (120) |
| n-Pr | n-Pr | H | 1 | 2 | cis | 14.1 ± 3.6 (72.8 ± 6.8) | 106 ± 3* | 90 ± 5* | 17.7 (53) | ** | 120.0 (20) |
| n-Pr | n-Pr | H | 1 | 2 | cis/trans | 20.3 ± 4.6 (64.0 ± 4.8) | 86 ± 4 | 65 ± 3 | 19 (30) | *** | 20.0 (30) |
| Theophylline | | | | | | 35.1 ± 5.3 (72.8 ± 6.6) | 132 ± 4 | 66 ± 8 | 18 (50) | *** | 94.0 (50) |
| Enprofylline | | | | | | 13.1 ± 3.1 (84.8 ± 3.6) | 120 ± 6 | 76 ± 10 | 48 (30) | *** | 93.0 (50) |
| Amrinone | | | | | | — | — | — | 4.12 (63) | | 77.0 (10) |

*Not significant.
**Unable to calculate due to minimal recovery; these agents caused minimal increases in blood pressure.
***Caused significant reduction in MABP below heart failure levels; therefore, RD$_{40}$'s could not be calculated.

What is claimed is:

1. A compound of the formula wherein
R$_1$ and R$_2$ may be the same or different and are selected from hydrogen, lower alkyl, allyl, carboxyalkyl, carbalkoxyalkyl and aralkyl,
R$_3$ is C=O;
n is 0 to 7 and
m is 1 to 7, with the proviso that n and m taken together cannot exceed 7;
and pharmaceutically acceptable salts of such compounds.

2. The compound of claim 1 wherein R$_1$ and R$_2$ are n-propyl, n is 1 and m is 2.

3. The compound of claim 1 wherein R$_1$ and R$_2$ are n-propyl and n and m are 2.